(12) United States Patent
Dal Molin et al.

(10) Patent No.: US 8,447,412 B2
(45) Date of Patent: May 21, 2013

(54) APPARATUS AND METHODS FOR WIRELESS COMMUNICATION VIA ELECTRICAL PULSES CONDUCTED BY THE INTERSTITIAL TISSUES OF THE BODY FOR AN ACTIVE IMPLANTABLE MEDICAL DEVICE

(75) Inventors: Renzo Dal Molin, Clamart (FR); Ashutosh Ghildiyal, Clamart (FR)

(73) Assignee: Sorin CRM S.A.S., Clamart Cedex (FR)

( * ) Notice: Subject to any disclaimer, the term of this patent is extended or adjusted under 35 U.S.C. 154(b) by 0 days.

(21) Appl. No.: 13/245,155

(22) Filed: Sep. 26, 2011

(65) Prior Publication Data

US 2012/0078322 A1   Mar. 29, 2012

(30) Foreign Application Priority Data

Sep. 24, 2010  (FR) ..................................... 10 57691

(51) Int. Cl.
*A61N 1/18* (2006.01)
(52) U.S. Cl.
USPC .............................. 607/60; 607/43

(58) Field of Classification Search
USPC ....................... 607/42–46, 32–37, 59–60, 5–9
See application file for complete search history.

(56) References Cited

U.S. PATENT DOCUMENTS

2003/0114899 A1* 6/2003 Woods et al. ................... 607/60

* cited by examiner

*Primary Examiner* — Carl H Layno
*Assistant Examiner* — Jon Eric C Morales
(74) *Attorney, Agent, or Firm* — Orrick Herrington & Sutcliffe, LLP

(57) ABSTRACT

An active implantable medical device having wireless communication of data via electrical pulses conducted by the interstitial tissues of the body. This device (12, 14) includes a pair of electrodes (22, 24) and generates pulse trains consisting of a series of electrical pulses applied to the electrodes. The pulse train is modulated by digital information (data) that is produced by the device. A regulated current or voltage source (42) is used to generate (44, 48) current or voltage pulses to form the pulse train. Each current or voltage pulse is a biphasic pulse comprising a positive and negative alternation. The biphasic current or voltage modulated by the digital information, is injected between the electrodes (22, 24) and wirelessly communicated.

13 Claims, 4 Drawing Sheets

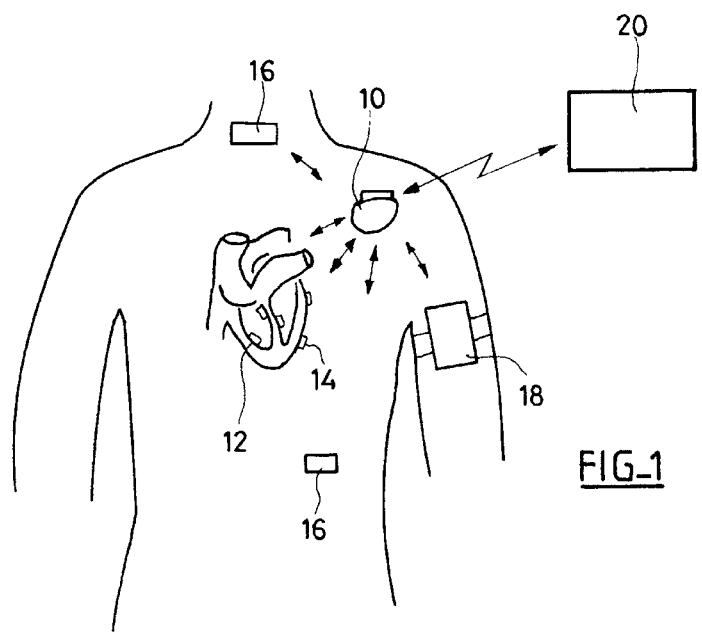
FIG_1
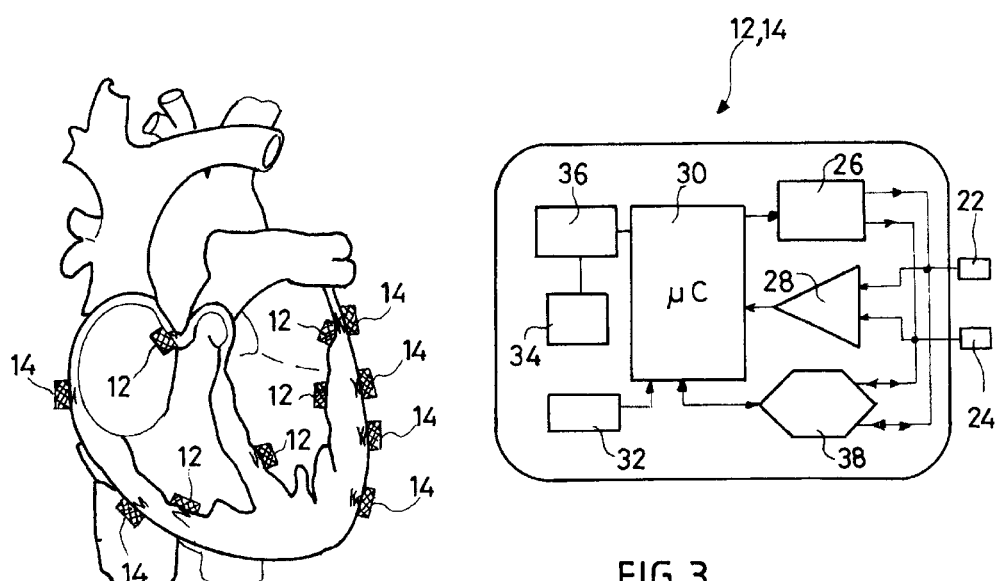
FIG_2
FIG_3

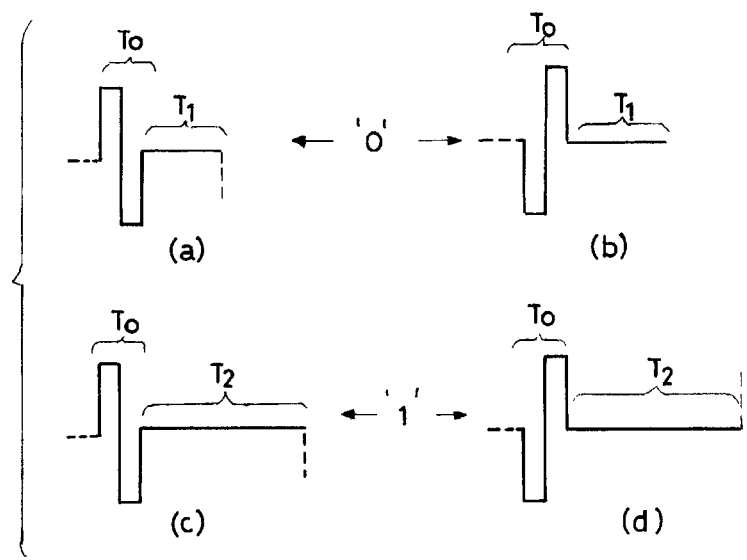
FIG_4
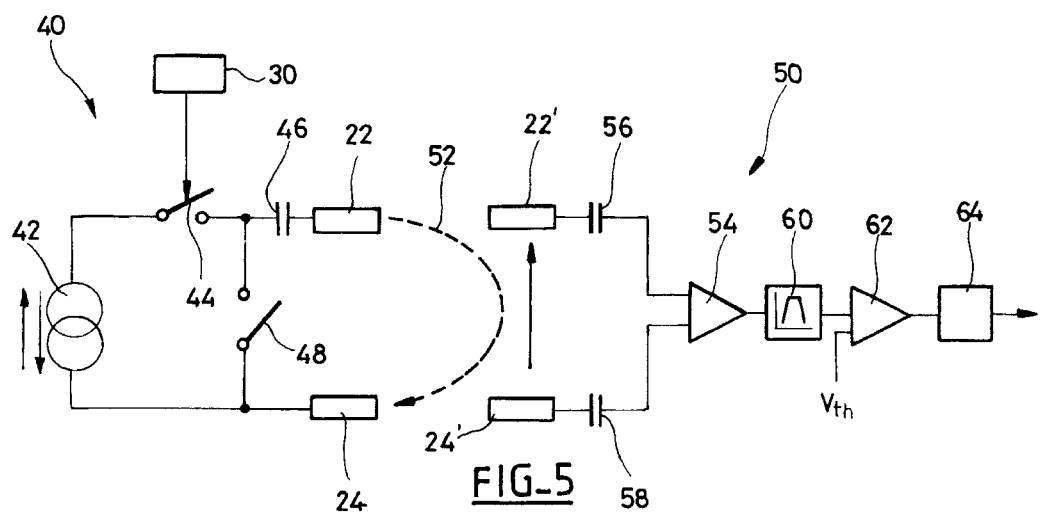
FIG_5

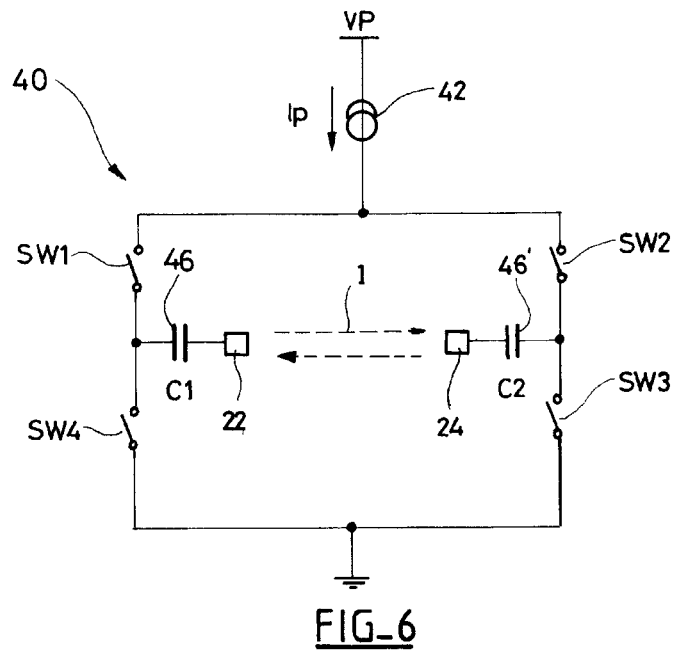
FIG_6
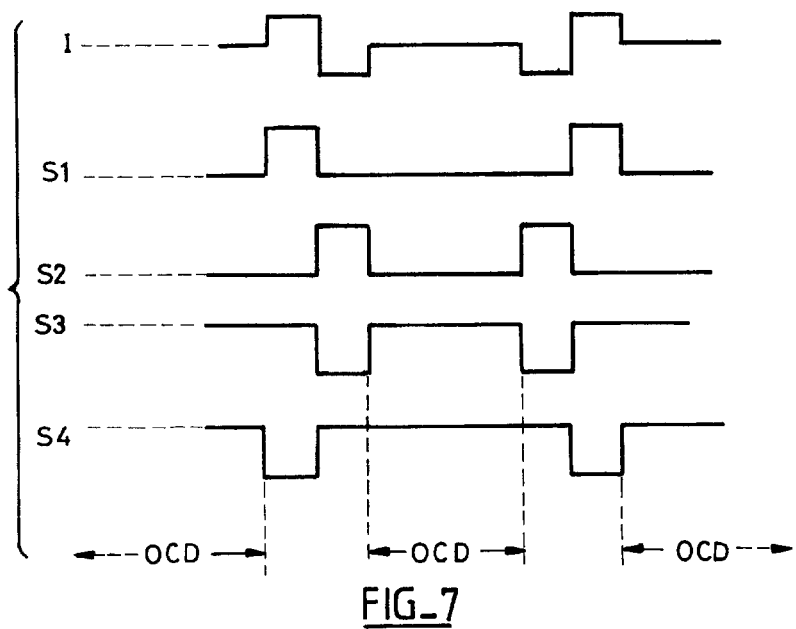
FIG_7

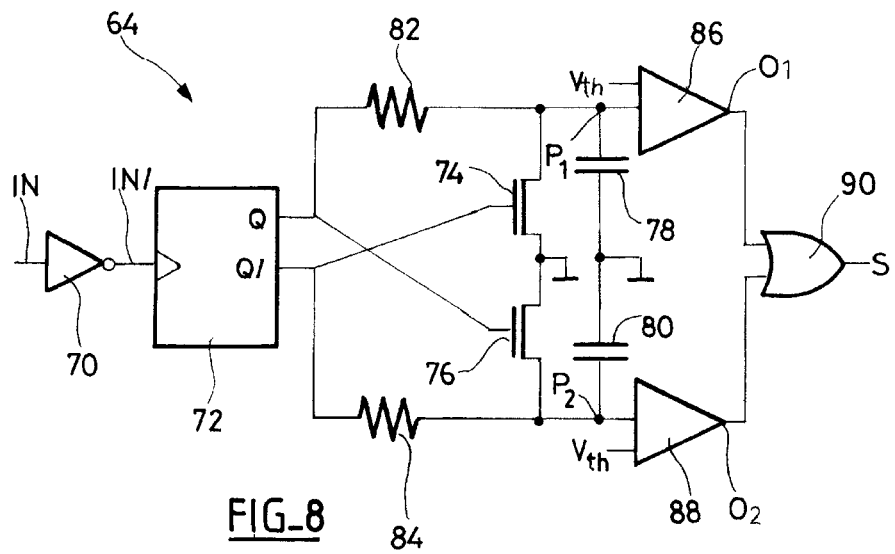
FIG_8
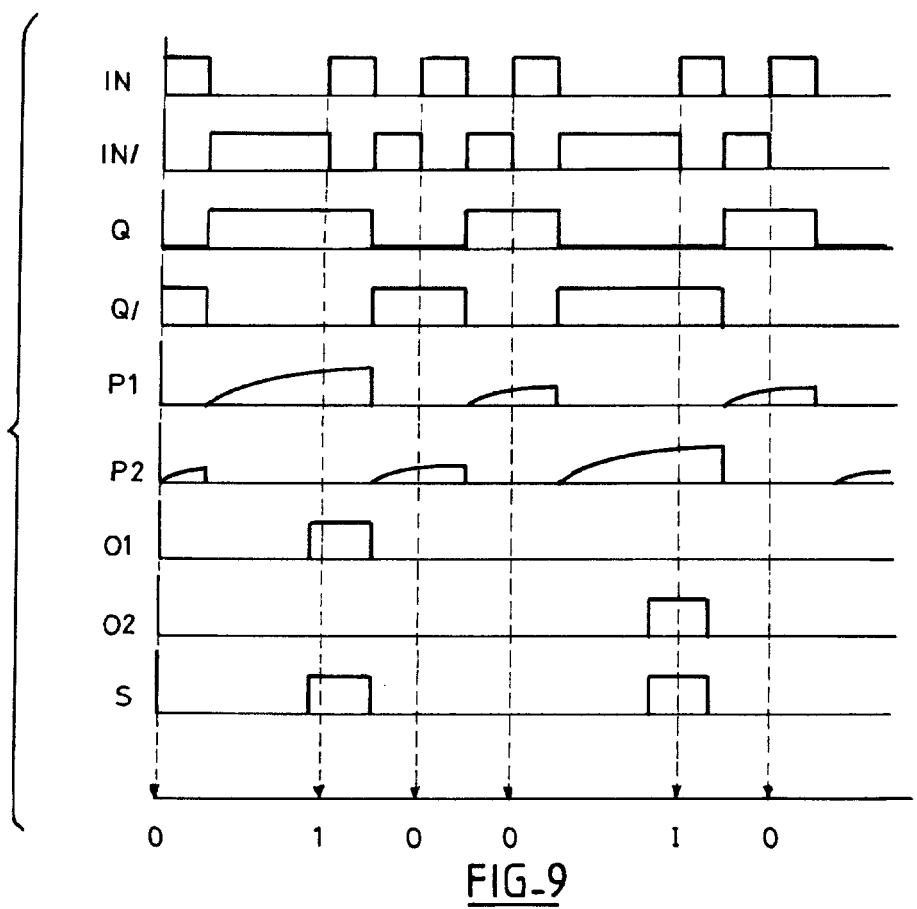
FIG_9

APPARATUS AND METHODS FOR WIRELESS COMMUNICATION VIA ELECTRICAL PULSES CONDUCTED BY THE INTERSTITIAL TISSUES OF THE BODY FOR AN ACTIVE IMPLANTABLE MEDICAL DEVICE

RELATED APPLICATIONS

The present application claims the benefit of French Application No. 1057691 entitled "Active Implantable Medical Device Comprising Means For Wireless Communication Via Electrical Pulses Conducted By The Interstitial Tissues Of The Body" and filed Sep. 24, 2010, which is hereby incorporated by reference in its entirety.

FIELD

The present invention relates to "medical devices" as defined by the 14 Jun. 1993 Directive 93/42/EEC of the Council of the European Communities, and more specifically to the "active implantable medical devices" as defined by the 20 Jun. 1990 Directive 90/385/EEC of the Council of the European Communities. Such medical devices include those that continuously monitor a patient's cardiac rhythm and deliver if necessary to the heart electrical pulses for causing stimulation, cardiac resynchronization, cardioversion and/or defibrillation, in response to a rhythm disorder detected by the device. They also include neurological devices, cochlear implants, etc., as well as devices for measuring a pH or an intracorporeal impedance measurement (for example, a transpulmonary impedance or an intracardiac impedance).

BACKGROUND

It is known to have active implantable medical devices that are implemented as autonomous capsules implanted in a patient without any physical connection to a remote device, which remote device may be either a main implanted device (e.g., housing of a stimulation pulse generator), or a main device that is not implanted (e.g., an external device such as a programmer or a device for remote monitoring of the patient). Communication of data between the autonomous capsule and the remote (main) device is by an intracorporeal path and can be conducted by the interstitial tissues of the body, and is known as Human Body Communication ("HBC"). For this reason the autonomous capsules are often referred to as "leadless capsules" (and referred to herein more simply as "capsules"), thereby to distinguish them from those implanted electrodes or sensors that are physically placed at the distal end of a lead, the lead being traversed throughout its length by one or more galvanic conductors connecting the electrode or sensor to a generator or other device connected at the opposite proximal end of the lead.

Known leadless capsules are for example described in U.S. Patent Publication No. 2007/0088397 A1 and PCT Publication WO 2007/047681 A2 (Nanostim, Inc.) or in the U.S. Patent Publication No. 2006/0136004 A1 (EBR Systems, Inc.). These leadless capsules can notably be epicardial capsules, attached to the outer wall of the heart, or endocardial capsules, fixed to the inner wall of a ventricular or atrial cavity. Their attachment to the heart wall is usually by a projecting helical anchoring screw, axially extending from the body of the capsule and designed to screw into and penetrate the heart tissue at the implantation site.

Such a capsule typically includes detection/stimulation circuits to collect depolarization potentials of the myocardium and/or to apply pacing pulses to the site where the capsule is implanted. Such a capsule then includes an appropriate electrode, which can conveniently be an active portion of the anchoring screw. It may also incorporate one or more sensors for measuring locally the value of a parameter such as, for example, the oxygen level in the blood, the endocardial cardiac blood pressure, the acceleration of the heart wall, and the acceleration of the patient as an indicator of activity. Of course, to enable an exchange of data to a remote device, these capsules also incorporate a transmitter/receiver for wireless communication.

Several techniques have been proposed for wireless communication between a leadless capsule and a remote device, for example, to allow the remote device to receive and centralize the information collected by a capsule and in turn send the capsule appropriate instructions, as necessary. The remote device may be, for example, an implanted pacemaker, resynchronizer or defibrillator, a subcutaneous defibrillator, or a long duration data recorder. As used herein, the term "data" should be understood to mean and include digital and/or analog signals representing measured parameter values, the status of the leadless capsule and its parameterization and functionality, and any other signals, instructions and information that is to be communicated between the leadless capsule and a remote (main) device.

U.S. Patent Publication No. 2006/0136004 A1 proposes to transmit the data by acoustic waves propagating inside the body. This technique is safe and effective; it nevertheless has the drawback of requiring a relatively high transmission power given the attenuation of acoustic waves passing through the body, and allows only relatively low data rates.

U.S. Pat. No. 5,411,535 proposes a different technique, based on the use of radiofrequency waves (RF) to transmit the data. Again, a relatively high transmission power is required, and attenuation of these waves by the intracorporeal tissues is a significant barrier to their propagation.

Another communication technique was proposed by U.S. Pat. No. 4,987,897, but it is a data exchange with an external main device (e.g., programmer) performed transdermally rather than intracorporeal. This transmission is ensured for short distances between, on the one hand, the housing of a pacemaker implanted in a subcutaneous pocket, and, on the other hand, an external programmer placed near this generator. The currents therefore circulate through the skin in a zone very distant from the sensitive areas, particularly at a great distance from the myocardium, which avoids any risk of disturbance of natural or stimulated depolarization waves of the myocardium.

U.S. Patent Publication No. 2007/0088397 A1 proposes to use the stimulation pulses produced by a capsule as a vehicle for the transmission of data previously collected or created by the capsule. To this purpose, the pulse, instead of presenting a monotonic variation of voltage, is interrupted in a controlled manner for very short durations in order to create the profile of the pulse of very narrow widths whose succession corresponds to binary encoding of the information to be transmitted. This technique allows using the high energy pacing pulses to overcome the problems of attenuation in the interstitial tissue between the capsule and the device. However, it has a number of drawbacks, including:

It is limited to transmitting data by an active capsule generating pulses: in the absence of generated pulses, it is not possible to transmit any data because the generated pulse is the carrier signal or the information vehicle;

It is restricted to continuous stimulation, because otherwise the system is unable to transmit streaming data, such as electrical signals collected by the capsule or values obtained by a sensor integrated into the capsule;

It is limited to one-way communication, from the active capsule producing the pulse to the remote receiving device, but not in the opposite direction;

It has a low data rate, limited to a few bits of information per pulse, and cannot transmit information at a rate higher than that of the stimulation pulses.

US Patent Publication No. 2002/0099423 A1 describes a wireless intracorporeal communication technique between an implanted medical device and an external device provided with electrodes in contact with the skin of the patient. The implanted device generates electrical pulse trains at a signal level that is below the cardiac stimulation threshold and delivers these pulses to electrodes to allow their propagation up to the surface of the patient's body. There, the signals are collected by the electrodes of the external device, and then decoded by the latter. This technique has several drawbacks, including a relatively high power consumption and a very high variability as a function of the load charge as seen from the implanted device between its electrodes for transmission of the pulses. Furthermore and above all, even with biphasic pulses (as described in this document), there is a high risk of residual charges, due to an imperfect balance of the positive and negative charges generated by the pulses. These residual charges produce a polarization in the tissues, thus creating a risk for the patient. For these reasons, this technique is not deemed appropriate for a permanent communication between medical devices, including communication between two implanted devices wherein the pulses would cross excitable regions of the myocardium. It is moreover proposed only for a transcutaneous communication between an implant and an external device, outside the dangerous zones. Furthermore, as it is a brief and temporary communication (the external device is, for example, used to collect from time to time the battery status of the implant), the relatively high energy consumption is not a critical factor.

OBJECT AND SUMMARY

It is therefore an object of the present invention to provide a wireless intracorporeal communication of data between an implantable medical device and a remote main device, typically between a leadless capsule (e.g., an implanted device that operates as a slave or client device) and an implanted leadless hub device (e.g., a remote device that operates as a main or master device relative to the leadless capsule(s), via the signals consisting of electrical pulses being conducted by interstitial tissues of the body, a technique that overcomes the aforementioned drawbacks of leadless capsule communications and provides the following benefits:

Possibility of communication with any type of leadless capsule,

Wireless communication that is totally safe for the patient, even in the case of signals passing through the myocardium tissue;

It requires little energy to establish communication, is particularly compatible with the relatively weak autonomy of the leadless capsules, and is dependent on an integrated self power supply system;

It permits transmission of high data rates;

It has no risk of interference by parasitic electrical signals present within the tissues of the body, including the disturbance due to myopotentials in the body.

To this end, the present invention is directed to an active implantable medical device of the type generally disclosed in US Patent Publication No. 2002/0099423 A1 cited above, incorporating intracorporeal wireless communication via electrical signals consisting of pulses conducted by the interstitial tissues of the body. The device includes at least one pair of electrodes, a generator circuit that generates a pulse train consisting of a series of electrical pulses and applies these pulses to the electrodes, and a modulator circuit that modulates the pulse train by digital information provided by the implanted device, the pulses being biphasic pulses comprising a positive and a negative alternation, and means for injecting the modulated biophasic pulses between the at least one pair of the electrodes.

The biphasic pulses may be voltage or current biphasic pulses, and preferably, the pulses are biphasic current pulses produced by a regulated current source included in the generator. More preferably, each positive and negative alternation of the voltage or current biphasic pulse has a waveform shape that is considered to be a square wave. The device thus communicates with at least one remote device, implanted or not, having circuits for receiving and decoding the modulated biphasic pulse train.

In one embodiment, the negative alternation of the biphasic pulse follows the positive alternation of the same pulse or vice versa; and more preferably, the positive and negative alternations of the biphasic pulse are symmetrical alternations.

In one embodiment, the pulses of the pulse train are generated with an alternation in the order of the polarity of the alternations of one biphasic pulse to the next, so that a biphasic pulse whose positive alternation precedes the negative alternation is followed by a consecutive negative alternation which precedes the following positive alternation and vice versa. Thus, a positive (negative) pulse can be followed by a negative (positive) pulse, followed by a negative (positive) pulse followed by a positive (negative) pulse, etc.

In one embodiment, the modulator circuit modulates the time interval between pairs of biphasic voltage or current pulses consecutive of the pulse train. In another embodiment, the modulator circuit modulates the width of the biphasic pulses. In yet another embodiment, the modulator circuit modulates the biphasic pulse magnitude. In still yet another embodiment, the modulator circuit modulates some combination of the foregoing parameters.

In a preferred embodiment, the duration of the biphasic current or voltage pulse is between 0.1 and 30 µs, more preferably about 0.5 µs, the recurrence period of the biphasic current or voltage pulses is between 2 µs and 2 ms, more preferably about 2 µs, and the amplitude of each of the positive and negative alternations of the current pulse is between 30 µA and 20 mA, more preferably about 10 mA.

It should be understood that the present invention is not limited to a particular type of leadless capsule, and it applies equally to wireless communication of data for any type of leadless capsule, regardless of its functional purpose between, for example, a leadless capsule and a remote main device and/or other leadless capsules.

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which like characters refer to like elements, and in which:

FIG. 1 schematically illustrates a set of medical devices including leadless capsules, implanted within the body of a patient;

FIG. 2 shows a plurality of leadless capsules implanted on the inner or outer wall of the myocardium;

FIG. 3 is a functional block schematic diagram of a leadless capsule;

FIG. 4 illustrates representative data waveforms for wireless communication in accordance with an embodiment of the present invention;

FIG. 5 is a schematic diagram of the transmitter and receiver elements in accordance with a preferred embodiment of the present invention;

FIG. 6 is a schematic diagram of a transmitter circuit for generating the biphasic current pulses of a preferred embodiment of the present invention;

FIG. 7 illustrates the timing sequences of the various switches of the circuit of FIG. 6;

FIG. 8 is a schematic diagram of a receiver circuit to decode the pulses generated by the transmitter circuit of FIG. 6;

FIG. 9 illustrates the timing of signals taken at different locations of the receiver circuit of FIG. 8.

DETAILED DESCRIPTION

With reference to the drawings, preferred embodiments of a system according to the present invention will now be described.

In FIG. 1, a set of active implantable medical devices implanted within the body of a patient, with each employing "HBC" (Human Body Communication, intracorporeal communication) for wireless communications is illustrated.

The patient is implanted with implantable device 10, such as a defibrillator/pacemaker/resynchronizer, a subcutaneous defibrillator, or a long-term event recorder. This implanted device 10 is considered for purposes of the present invention as a (main) master device of a network comprising a plurality of implantable slave devices 12 to 18 with which it is capable of communicating by HBC. The main device 10 is said to be remote relative to the plurality of slave devices 12 to 18. The slave devices 12 and 18 may include intracardiac 12 or epicardial 14 leadless capsules implanted directly onto the patient's heart, other devices 16 such as myopotential sensors or neurological stimulation devices, and possibly an external device 18 disposed on an armband and provided with electrodes in contact with the patient's skin. Main device 10 also can be used as a gateway to the outside world to communicate with an external device 20, such as a programmer or a data transmission device, via, for example, RF telemetry in the Medical Implants Communication System ("MICS") frequency band 402-405 MHz, or the unmarked public Industrial, Scientific and Medical ("ISM") frequency bands 863-870 MHz, 902-928 MHz and 2.4 GHz conventionally used by medical devices.

Each of the devices 10 to 18 is provided with at least one pair of electrodes which are either in direct contact with the tissues of the body (as is the case for the implanted devices), or in contact with the skin (as is the case for the external device 18).

In FIG. 2 an example of leadless capsule implanted either on the anterior part of the myocardium, within an atrial or ventricular cavity (endocardial capsules 12) or on an outer wall of the same myocardial (epicardial capsules 14) is shown. These capsules, which are described in more detail, for example, in U.S. Patent Publication No. 2007/0088397 A1, WO 2007/047681 A2 and U.S. Patent Publication No. 2006/0136004 A1 above, are attached to the heart wall using a projecting anchoring screw for penetrating into the cardiac tissue by screwing at the implant site. The screw can either be a passive screw, serving only for fixing the capsule, or an active screw, for collecting the signals of depolarization that propagate in the myocardium tissue and/or for delivering localized stimulation pulses (e.g., pacing pulses) to the implantation site.

FIG. 3 schematically shows the different internal circuits of a representative slave device that is leadless capsule 12, 14 (and, mutatis mutandis, of the other implanted elements designed to wirelessly communicate with each other and or the main device 10 according to the present invention). Each capsule 12 contains a pair of electrodes 22, 24, one of which may also be constituted by the anchoring screw in the heart tissue. These electrodes are connected to a pacing pulse generator circuit 26 (for an active capsule incorporating this function) and/or a detection circuit 28 for the collection of depolarization potentials collected between the electrodes 22 and 24. A central processing unit (CPU) circuit 30 provides control of the various functions, e.g., processing and memorization of the collected signals in a memory. The capsule can also be equipped with a sensor 32 for acquiring a patient parameter such as, for example, one or more of an acceleration sensor, a pressure sensor, a hemodynamic sensor, a temperature sensor, and an oxygen saturation sensor. The capsule is powered by a small battery or by an energy harvester circuit 34 supplying all the circuits via a power management stage 36. Examples of energy harvesters: US 2006/0217776 A1, U.S. Pat. No. 3,456,134 A, WO 2007/149462 A2, US 2005/0256549 A1, GB 2 350 302 A, US 2008/0262562 A1, US 2007/0276444 A1.

Characteristically of the present invention, the electrodes 22 and 24 are, in all cases, also connected to a modulator/demodulator circuit 38 that is in turn coupled to CPU circuit 30 for transmitting and/or receiving pulses used for the wireless HBC communication. These pulses have characteristics specific to the invention that are described below.

Depending on whether the stimulation circuit (module 26) and the detection circuit (module 28) are present or not, the electrodes 22, 24 may provide a single, double or triple function, namely stimulation and/or collection of cardiac potentials (if applicable) and/or transmission of data tracked by sensor 32 (if applicable), and in any event transmission/reception for the HBC communication.

CPU circuit 30 preferably includes all the electronics for controlling the various functions of the leadless capsule 12. It includes a microcontroller and an oscillator for generating clock signals required for operation of the microcontroller and for communication. It may also contain an analog to digital converter, a digital to analog converter, and a digital storage memory.

FIG. 4 illustrates an example of a pulse produced by the circuit 38 for HBC communication through electrical pulses conducted through the interstitial tissues of the body. In accordance with the present invention, (i) these pulses may be current or voltage pulses, and (ii) each generated pulse is a biphasic pulse to minimize the residual charge injected into the heart and/or to reduce the material corrosion.

In the examples shown in FIG. 4, these pulses consist of two successive symmetrical positive and negative alternations of square wave signals. As used herein, the term "square wave" means with the same magnitude in absolute terms, and with the same duration, for both positive and negative alternations. It should be understood that other waveform shapes may be used, however, and the embodiment described herein using a square wave should not be considered as exhaustive or limiting.

Also in this example, the modulation of pulses results from the variable temporal interval between pairs of consecutive current pulses of a biphasic pulse train generated by the device. Each pulse is defined by the succession of two alternations of opposite sign of constant duration $T_0$. This pulse is followed by a short temporal interval $T_1$ respectively, to encode for example a '0' bit, or a long temporal interval $T_2$, to encode a '1' bit.

Other types of modulation are possible, however, such as a pulse amplitude modulation or an alternation pulse width modulation (PWM modulation).

The biphasic pulse may have a positive alternation followed by a negative alternation (FIGS. 4a and 4c) or a negative alternation followed by a positive alternation (FIGS. 4b and 4d).

Advantageously, to minimize the residual charges that may result from imperfections of a biphasic pulse which is not well balanced, after having emitted a pulse of a first type (e.g., a positive alternation followed by a negative alternation, as in FIGS. 4a and 4c), the next pulse can be a pulse of opposite type (e.g., a negative alternation followed by a positive alternation, as in FIGS. 4b and 4d), or not of opposite type.

This allows exactly compensating the injection of any residual charge for each bit of information sent, therefore respecting the medical standards and ensuring the safety of emitted pulses.

An error detection technique by a verification of the systematic presence of the known alternating pattern in the received pulse train also can be implemented on the receiver side.

The biphasic pulses are preferably emitted in succession as a train of pulses at a relatively high frequency, typically at a rate of one bit every 2 microseconds. The duration $T_0$ of the pulse is about 1000 ns, a value that is suitable for efficient transmission within the human body.

Choosing a repetition rate of about 500 kHz (1 bit every 2 µs on average) allows adjusting the spectral content to the particular transmission channel formed by the interstitial tissues of the body, which has a relatively moderate minimum attenuation in the band 500 kHz-10 MHz (B band). In general, the attenuation in this frequency band varies between 10 dB and 40 dB, depending on the distance between the transmitter and the receiver, with the spacing between the respective electrodes of the pair of electrodes and with the surface of these electrodes, with a typical value around 20 dB at 1 MHz over a distance of 10 to 12 cm between the transmitter and the receiver.

FIG. 5 schematically illustrates the circuit schematics used to transmit and receive the biphasic pulses as described above. In one embodiment, the circuits of the transmitter 40 are located in the slave device 12, for example, a leadless capsule containing a pacemaker, or in main device 10, for example, the subcutaneous device, each of which device monitors the cardiac activity and generates stimulation, resynchronization, defibrillation and/or cardioversion pulses. Transmitter 40 includes a constant regulated current source 42 of about 10 mA, adjustable periodically or on command, depending on the resistance of the lead connected to the heart, to generate at the end of the pulse a voltage of 2 V for example. The CPU module 30 is programmed to control the opening and closing of switches 44, and 48, especially the closure of the switch 44, to inject the current for a predetermined time interval, e.g., about 0.5 microseconds. The injected current 52 circulates (via the coupling capacitor 46, shared or not with the stimulation stage, to avoid sending any voltage on the electrodes) through the patient's body from one of the electrodes 22 to the other electrode 24. The switch 48 can then be closed to discharge the capacitor 46 of the residual charge due to the compensation errors of the positive and negative pulses.

Having thus injected a first alternation, the same method is used by reversing the current direction to inject the following alternation, to produce thereby a pulse of the type illustrated in FIG. 4.

The reference 50 generally designates the receiver circuits used on the receiving side of the communication technique of the present invention. The current 52 circulating in the body generates between the electrodes 22' and 24' of the receiver 50, a potential difference that is applied to an amplifier stage 54 via coupling capacitors 56 and 58 to eliminate any DC component. The amplifier stage 54 is powered only during periods when data are to be obtained to reduce the current consumption. The resulting amplified signal is applied to a bandpass filter 60, to filter out unwanted signals outside the relevant frequency band. The resulting filtered signal is applied to a threshold comparator 62 and to a demodulator stage 64 (these circuits are described in more detail below with reference to FIGS. 8 and 9).

FIGS. 6 and 7 illustrate a principle schematic diagram of a biphasic current generator. The constant current source 42 is connected to the electrodes 22 and 24 by two switches SW1 and SW2 and by the coupling capacitors 46 and 46', which are connected to ground through two switches SW3 and SW4. FIG. 7 shows the timing diagrams of different control signals S1 to S4 respectively applied to switches SW1 to SW4 (the switch being closed when the signal is in high state). FIG. 7 also shows the profile of the current I circulating between the two electrodes 22 and 24. On this timing diagram, two successive symmetrical biphasic pulses, with reversal of the sequence of alternations of one pulse to the next (positive-then-negative, negative-then-positive), are shown. Finally, the referenced period OCD corresponds to the discharge of output capacitors, which is operated through the switches SW3 and SW4. In case the capacitors 46 and 46' are shared with the stimulation stage, the OCD discharge is performed in refractory period only, because of its longer duration.

FIG. 8 illustrates an exemplary receiver circuit 64 which includes a demodulator to decode pulses such as those generated by the circuits described above and as illustrated in FIG. 4, that is to say for signals which binary encoding '0' or '1' corresponds to a respectively short waiting time $T_1$ or long waiting time $T_2$ from one pulse to the next. The demodulator 64 receives data IN from the comparator 62. The data IN are then applied to an inverter 70 whose output IN/controls a flip-flop 72 whose output Q and the complementary output Q/ are respectively connected to the gates of the symmetrical transistors 74 and 76. Each of these transistors charges a capacitor 78 or 80 by a resistor 82 or 84. The voltage at the common point P1 or P2 each set of capacitor-resistor is applied to the input of a respective comparator 86 or 88 whose other input is connected to a threshold reference voltage $V_{th}$. The $O_1$ and $O_2$ outputs of the comparators 86 and 88 are applied to an OR circuit 90 whose output S is such that when the load of either capacitor 78 or 80 reaches the threshold value $V_{th}$, the demodulator 64 sends an output pulse O, which goes to zero with the falling edge of input signal IN.

As can be seen from the waveforms in FIG. 9, the last line in the FIG. 9 shows the decoded binary word '010010'.

One skilled in the art will appreciate that the present invention may be practiced by other than the embodiments described above, which are presented for purposes of illustration and not of limitation.

The invention claimed is:
1. An active implantable medical device, comprising means for wireless intracorporeal communication with at least one other active implantable medical device via electrical signals conducted by the interstitial tissues of a patient's body comprising:
- Means for providing digital information to be communicated;
- at least one pair of electrodes
- Means for generating a pulse train containing a succession of electrical pulses, said generator means comprising a regulated current source, wherein said pulse train comprises a train of biphasic current pulse produced by said regulated current source, each biphasic pulse comprising a positive and a negative alteration;
- Means for modulating the pulse train by said digital information; and
- Means for injecting the modulated pulse train between said at least one pair of electrodes;
- wherein the modulation means further comprises means for modulating a temporal interval between the pairs of consecutive biphasic current pulses of the biphasic pulse train.

2. The device of claim 1, wherein each positive and negative alternation of a biphasic current pulse comprises a square wave shape.

3. The device of claim 1, wherein the negative alternation of the biphasic current pulse follows the positive alternation of that pulse, or vice versa.

4. The device of claim 1, wherein the negative and positive alternations of said biphasic current pulse are symmetrical.

5. The device of claim 1, wherein said pulse train comprises an alternation of the sequence of polarities of the alternations from one biphasic pulse to the next, so that a biphasic pulse whose positive alternation precedes the negative alternation is followed by a biphasic pulse whose negative alternation precedes the positive alternation, and vice versa.

6. The device of claim 1, wherein the modulation means further comprises means for modulating the pulse width of successive biphasic current pulses of the pulse train.

7. The device of claim 1, wherein the modulation means further comprises means for modulating an amplitude of the successive biphasic current pulses of the pulse train.

8. The device of claim 1, wherein the biphasic current pulse has a duration between 0.1 and 30 µs.

9. The device of claim 8, wherein the biphasic current pulse has a duration of 0.5 µs.

10. The device of claim 1, wherein the biphasic current pulse has a recurrence period of between 2 µs and 2 ms.

11. The device of claim 10, wherein the recurrence period is 2 µs.

12. The device of claim 1, wherein the positive and negative alternation of the current pulse each has an amplitude of between 30 µA and 20 mA.

13. The device of claim 12, wherein the amplitude is 10 mA.

* * * * *